(12) United States Patent
Barker et al.

(10) Patent No.: US 8,377,665 B2
(45) Date of Patent: *Feb. 19, 2013

(54) ALCOHOL PRODUCTION PROCESS

(75) Inventors: Will David Barker, Auckland (NZ);
Jason Carl Bromley, Auckland (NZ);
Christophe Daniel Mihalcea, Auckland (NZ)

(73) Assignee: LanzaTech New Zealand Limited, Auckland (NZ)

(*) Notice: Subject to any disclaimer, the term of this patent is extended or adjusted under 35 U.S.C. 154(b) by 0 days.

This patent is subject to a terminal disclaimer.

(21) Appl. No.: 13/119,582

(22) PCT Filed: Jan. 14, 2011

(86) PCT No.: PCT/NZ2011/000002
§ 371 (c)(1),
(2), (4) Date: Jul. 12, 2011

(87) PCT Pub. No.: WO2011/087380
PCT Pub. Date: Jul. 21, 2011

(65) Prior Publication Data
US 2011/0269197 A1    Nov. 3, 2011

Related U.S. Application Data

(60) Provisional application No. 61/295,145, filed on Jan. 14, 2010.

(51) Int. Cl.
*C12P 7/40* (2006.01)
(52) U.S. Cl. .......................... 435/136; 435/41; 435/155
(58) Field of Classification Search .................. None
See application file for complete search history.

(56) References Cited

U.S. PATENT DOCUMENTS

| | | | |
|---|---|---|---|
| 5,173,429 A | 12/1992 | Gaddy et al. | |
| 5,593,886 A | 1/1997 | Gaddy | |
| 5,807,722 A | 9/1998 | Gaddy | |
| 5,821,111 A | 10/1998 | Grady et al. | |
| 6,136,577 A | 10/2000 | Gaddy | |
| 6,340,581 B1 | 1/2002 | Gaddy | |
| 6,368,819 B1 | 4/2002 | Gaddy et al. | |
| 6,753,170 B2 | 6/2004 | Gaddy et al. | |
| RE39,175 E | 7/2006 | Gaddy et al. | |
| 7,196,218 B2 | 3/2007 | Gaddy et al. | |
| 7,285,402 B2 | 10/2007 | Gaddy et al. | |
| 2007/0275447 A1 | 11/2007 | Lewis et al. | |
| 2009/0317882 A1 | 12/2009 | Cheng et al. | |
| 2010/0323417 A1 | 12/2010 | Simpson et al. | |

FOREIGN PATENT DOCUMENTS

| | | |
|---|---|---|
| WO | WO02097106 A1 * | 10/2002 |
| WO | 02/097106 | 12/2002 |
| WO | WO02097106 * | 12/2002 |
| WO | 2007/117157 | 10/2007 |
| WO | 2008/028055 | 3/2008 |
| WO | 2008/154301 | 12/2008 |
| WO | 2009/020747 | 2/2009 |
| WO | 2009/022925 | 2/2009 |
| WO | 2009/058028 | 5/2009 |
| WO | 2009/072887 | 6/2009 |
| WO | 2009/113878 | 9/2009 |
| WO | 2010/064932 | 6/2010 |
| WO | 2010/064933 | 6/2010 |
| WO | 2010/093262 | 8/2010 |
| WO | 2010/098679 | 9/2010 |
| WO | 2011/002318 | 1/2011 |

OTHER PUBLICATIONS

Wood et al., 1991, Life with CO or CO2 and H2 as a source of carbon and energy, FASEB Journal 5: 156-163.*
Phillips, J.R., et al. "Synthesis Gas as Substrate for the Biological Production of Fuels and Chemicals." Applied Biochemistry and Biotechnology, 1994, 45/46. pp. 145-157.
Abrini J. et al. "*Clostridium autoethanogenum*, sp. Nov., an Anaerobic Bacterium that Produces Ethanol from Carbon Monoxide", Archives of Microbiology. 1994, vol. 161, pp. 345-351.
Ragsdale, S.W. "Life with Carbon Monoxide." Critical Reviews in Biochemistry and Molecular Biology, 2004, 39, pp. 165-195.
Henstra, et al. "Microbiology of Synthesis Gas Fermentation for Biofuel Production." Current Opinion in Biotechnology, 2007, 18, pp. 200-206.

* cited by examiner

*Primary Examiner* — Ralph Gitomer
*Assistant Examiner* — Robert Yamasaki
(74) *Attorney, Agent, or Firm* — Frank S Molinaro

(57) ABSTRACT

The invention relates to methods for improving the efficiency of carbon capture in microbial fermentation of a gaseous substrate comprising CO and/or H2. In certain aspects the invention relates to improving the efficiency of carbon capture in the microbial fermentation of gaseous substrate comprising CO and/or H2 to produce alcohol(s) and/or acid(s). In particular the invention relates to methods for improving the efficiency of carbon capture in carboxydotrophic fermentation.

7 Claims, 1 Drawing Sheet

ALCOHOL PRODUCTION PROCESS

CROSS REFERENCE TO RELATED APPLICATIONS

This application is a National Stage of International Application No. PCT/NZ2011/000002, filed on Jan. 14, 2011, which claims priority to U.S. Provisional Application No. 61/295,145 filed Jan. 14, 2010. The contents of the prior applications mentioned above are incorporated herein by reference.

FIELD OF THE INVENTION

This invention relates generally to methods for producing products, particularly alcohols, by microbial fermentation. In particular, the invention relates to methods for improving the efficiency of carbon capture in carboxydotrophic fermentation.

BACKGROUND OF THE INVENTION

Ethanol is rapidly becoming a major hydrogen-rich liquid transport fuel around the world. Worldwide consumption of ethanol in 2005 was an estimated 12.2 billion gallons. The global market for the fuel ethanol industry has also been predicted to continue to grow sharply in future, due to an increased interest in ethanol in Europe, Japan, the USA and several developing nations.

For example, in the USA, ethanol is used to produce E10, a 10% mixture of ethanol in gasoline. In E10 blends, the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, and the cultivation of starch or sucrose-producing crops for ethanol production is not economically sustainable in all geographies. Therefore, it is of interest to develop technologies to convert lower cost and/or more abundant carbon resources into fuel ethanol.

CO is a major, free, energy-rich by-product of the incomplete combustion of organic materials such as coal or oil and oil derived products. For example, the steel industry in Australia is reported to produce and release into the atmosphere over 500,000 tonnes of CO annually.

Catalytic processes may be used to convert gases consisting primarily of CO and/or CO and hydrogen ($H_2$) into a variety of fuels and chemicals. Micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as a sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. While using CO as the sole carbon source, all such organisms produce at least two of these end products.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Abrini et al., Archives of Microbiology 161, pp 345-351 (1994)).

However, ethanol production by micro-organisms by fermentation of gases is always associated with co-production of acetate and/or acetic acid. As some of the available carbon is converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to GHG emissions.

Several enzymes known to be associated with the ability of micro-organisms to use carbon monoxide as their sole source of carbon and energy are known to require metal co-factors for their activity. Examples of key enzymes requiring metal cofactor binding for activity include carbon monoxide dehydrogenase (CODH), and acetyl —CoA synthase (ACS).

WO2007/117157, WO2008/115080, WO2009/022925, WO2009/058028, WO2009/064200, WO2009/0164201 and WO2009/113878, the disclosure of which are incorporated herein by reference, describe processes that produce alcohols, particularly ethanol, by anaerobic fermentation of gases containing carbon monoxide. Acetate produced as a by-product of the fermentation process described in WO2007/117157 is converted into hydrogen gas and carbon dioxide gas, either or both of which may be used in the anaerobic fermentation process. WO2009/022925 discloses the effect of pH and ORP in the conversion of substrates comprising CO to products such as acids and alcohols by fermentation. WO2009/058028 describes the use of industrial waste gases for the production of products, such as alcohol, by fermentation. WO2009/064201 discloses carriers for CO and the use of CO in fermentation. WO2009/113878 discloses the conversion of acid(s) to alcohol(s) during fermentation of a substrate comprising CO.

Fermentation of substrates comprising CO and/or CO2 require energy (typically referred to as 'reducing equivalents') to fix carbon into microbial cell mass and/or products such as ethanol. The reducing equivalents required for the fixation of carbon into cell mass and products are typically derived through the oxidation of CO and/or H2. In the absence of H2, all reducing equivalents are derived from the oxidation of CO to CO2. When hydrogen is available, at least a portion of the H2 can be used to produce reducing equivalents and less CO is required to be oxidised to $CO_2$. In extreme case, where an abundance of H2 is available, all the carbon in CO and/or $CO_2$ can be fixed into cell mass and products such as alcohols and the reducing equivalents can all be derived from H2. When $CO_2$ is produced, it represents an inefficiency in carbon capture, as it is expelled from the fermentation system, rather than being fixed. It is an object of the present invention to provide a process that goes at least some way towards overcoming the above disadvantages, or at least to provide the public with a useful choice.

SUMMARY OF THE INVENTION

In a first broad aspect of the invention, there is provided a method of improving efficiency of carbon capture in carboxydotrophic fermentation via the Wood-Ljungdahl pathway, the method including applying an electrical potential across the fermentation. In particular embodiments, carbon is captured via fixation of CO and/or CO2 into cell mass and/or products.

In particular embodiments, the products produced by fermentation are acids and/or alcohols.

In a second broad aspect, there is provided a method of increasing microbial growth of a micro-organism in fermentation of a substrate comprising CO, the method including applying an electrical potential across the fermentation.

In particular embodiments, microbial growth rate increase by at least 5%. In particular embodiments, microbial growth rates increase by at least 10%. In particular embodiments, microbial growth rates increase by at least 15%. In particular embodiments, microbial growth rates increase by at least 20%.

In particular embodiments of the first and second aspects, a potential is applied across the fermentation by electrolysis. In particular embodiments, electrolysis includes passing a direct current with a voltage of up to 20V across two electrodes. In particular embodiments, a potential of at least 2V, or at least 4V, or at least 6V, or at least 8V, or at least 10V, or at least 15V, or at least 20V is applied. In particular embodiments of the invention, the potential can be controlled such that a substantially constant current through the electrolyte is maintained at approximately 1 mA, or approximately 2 mA, or approximately 3 mA, or approximately 4 mA, or approximately 5 mA, or approximately 6 mA, or approximately 7 mA, or approximately 8 mA, or approximately 9 mA, or approximately 10 mA.

In particular embodiments of the first and second aspects, the method includes adding one or more electron shuttle mediator(s) to the fermentation broth. Alternatively, the fermentation can be conducted without one or more electron shuttle mediators.

In another aspect of the invention there is provided a method of fermentation of a substrate comprising CO and/or H2, wherein at least a portion of the CO and/or H2 are used to produce one or more reducing equivalents. The method according to this aspect of the invention includes providing one or more electrons to the fermentation such that the amount of CO and/or H2 used to produce said one or more reducing equivalents can be decreased or mitigated.

Embodiments of the invention find particular application in the production of acids and alcohols, particularly ethanol by fermentation of a gaseous substrate comprising CO. The substrate may comprise a gas obtained as a by-product of an industrial process. In certain embodiments, the industrial process is selected from the group consisting of ferrous metal products manufacturing, non-ferrous products manufacturing, petroleum refining processes, gasification of biomass, gasification of coal, electric power production, carbon black production, ammonia production, methanol production and coke manufacturing. In one embodiment of the invention, the gaseous substrate is syngas. In one embodiment, the gaseous substrate comprises a gas obtained from a steel mill.

In particular embodiments of the first and second aspects, the CO-containing substrate will typically contain a major proportion of CO, such as at least about 20% to about 100% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when $H_2$ and $CO_2$ are also present.

In various embodiments, the fermentation is carried out using a culture of one or more strains of carboxydotrophic bacteria. In various embodiments, the carboxydotrophic bacterium is selected from *Clostridium, Moorella, Oxobacter, Peptostreptococcus, Acetobacterium, Eubacterium* or *Butyribacterium*. In one embodiment, the carboxydotrophic bacterium is *Clostridium autoethanogenum*.

In another embodiment of the invention, there is provided an electrochemical bioreactor comprising means for introducing a substrate comprising CO and/or CO2 and optionally H2 to a fermentation broth and means for applying a potential across the fermentation broth. In particular embodiments, the means for applying a potential is controllable, such that a desired current can be maintained through the fermentation broth.

In particular embodiments, the electrochemical bioreactor is configured such that the fermentation broth can be maintained in a half-cell. In particular embodiments, the half-cell excludes oxygen.

The invention may also includes the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

DETAILED DESCRIPTION OF THE INVENTION

Figure 1:
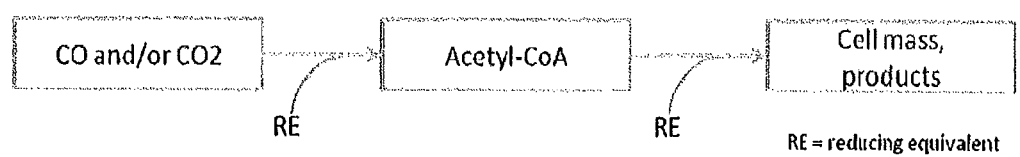
FIG. 1 is a schematic overview of the conversion of CO and/or CO2 to cell matter and products via the Wood-Ljungdahl pathway.

In accordance with the invention, there is provided a method of improving efficiency of carbon capture in fermentation via the Wood-Ljungdahl pathway, the method including applying an electrical potential across the fermentation. In particular embodiments, carbon is captured via fixation of CO and/or CO2 into cell mass and/or products. In particular embodiments, carboxydotrophic micro-organism are used in the fermentation. In particular embodiments, the products produced by fermentation are acids and/or alcohols. For example, fermentation of carbon containing substrate by *Clostridium autoethanogenum* produces products including acetate and ethanol. Typically, substrates comprising CO and/or CO2 are converted to cell matter and products via the Wood-Ljungdahl pathway as simplistically represented in FIG. 1. For the purpose of the present invention reducing equivalents can be defined as biological reducing energy such as NADH or similar. Reducing equivalents are used in cellular processes such as fermentation to fix carbon into product(s) and cell mass, and are used as reducing power for producing and reducing metabolites formed in the fermentation.

As would be understood by a person skilled in the art, fermentation is a process that allows cells to obtain energy from the oxidation of organic compounds. In anaerobic conditions, fermentation allows respiration to occur in the absence of oxygen. There are a number of well known anaerobic fermentation processes including ethanol fermentation, lactic acid fermentation and glycolysis. Fermentation of substrates comprising CO and/or CO2 via the Wood Ljungdahl pathway requires energy to fix carbon into cell mass and/or products. Reducing equivalents provide the energy required for these reactions. The fermentation of a substrate comprising CO can produce product(s) including but not limited to alcohol(s) and/or acid(s). Examples of the metabolites formed by such a fermentation include but are not limited to acids; such as acetate, propionate, butyrate, lactate, acrylate; and other products such as ethanol, acetone, propanol, butanol and 2,3 butanediol.

Reducing equivalents are derived from H2 or CO through (i) Hydrogenase or (ii) Water Gas Shift Reactions:

$$NAD^+ + H_2 \rightarrow NADH + H^+ \quad (i)$$

$$CO + H_2O \rightarrow CO_2 + H_2 \quad (ii)$$

The following (non-limiting) example demonstrates the requirement for reducing equivalents (RE) in the conversion of CO to ethanol ($CH_3CH_2OH$).

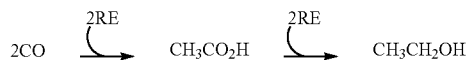

$$2CO \xrightarrow{2RE} CH_3CO_2H \xrightarrow{2RE} CH_3CH_2OH$$

As can be seen in the above equation, the conversion of CO to ethanol requires two carbon molecules as provided by the 2CO shown. Two reducing equivalents are required for the carbon fixation and reduction of CO to $CH_3CO_2H$. A further two reducing equivalents are required for the reduction of $CH_3CO_2H$ to $CH_3CH_2OH$. The requirements for these reducing equivalents are met in the following stoichiometry;

$$6CO + 3H_2O \rightarrow CH_3CH_2OH + 4CO_2$$

In this instance the reducing equivalents are being derived from CO by way of the water gas shift reaction. In accordance with an aspect of the current invention, at least a portion of the reducing equivalents required to fix CO and/or CO2 is provided electrically. Without wishing to be bound by theory, it is considered that applying a potential across a fermentation can result in regeneration of reducing power or reducing equivalents, such that they are available for cellular reduction reactions required to fix carbon. In particular embodiments, electrons are provided to one or more micro-organisms to reduce the amount of CO and/or H2 required to fix carbon into cell mass and/or products. Correspondingly as the amount of CO required to fix carbon into cell mass and/or products is decreased, the amount of CO2 produced as a by product of the reaction also decreases. In particular embodiments, the electrons are provided by electrolysis.

In known electrochemical carbohydrate fermentations, electrons are typically made available using electron shuttle mediators, such as methyl viologen, benzyl viologen or neutral red. Examples of such fermentations are detailed in Zeikus et al., Applied Microbiology and Biotechnology, 2002, 58: 476-481 and references therein, which are fully incorporated herein by reference. In particular embodiments of the invention, the electrons are provided without the need of electron shuttling mediators. Without wishing to be bound by theory, it is considered one or more media components described in the examples section herein may act as an electron shuttle.

It has also be surprisingly recognised that when a potential is applied across a fermentation, the metabolism of the micro-organism(s) can change. In particular embodiments of the invention, application of a potential results in an increase in microbial growth. In particular embodiments, microbial growth rate increase by at least 5%, or at least 10%, or at least 15%, or at least 20%. As such, the invention provides a method for increasing growth rate of a micro-organism. It is noted that there may be a slight reduction in metabolite production as a result in shift in carbon fixation metabolism.

Furthermore, it is recognised that during fermentation, there may be stages wherein microbial growth is a priority, such as during start-up. During this stage, a potential can be applied across the fermentation such that the growth rate increases. During stages of fermentation wherein product formation is the priority, the potential can be reduced to removed.

In another aspect, the invention provides an electrochemical bioreactor comprising means to provide a substrate comprising CO and/or CO2 to one or more micro-organisms and means to provide electrons to one or more micro-organisms. Carboxydotrophic micro-organisms are usually anaerobic and fermentation of substrate comprising CO and/or CO2 are typically provided in gaseous form. Fermentation of substrates comprising CO and/or CO2 can be conducted in a bioreactor containing a fermentation broth comprising one or more micro-organisms and essential nutrients required for cell growth and metabolism. In accordance with the invention, electrons can be provided to the micro-organisms by applying an electrical potential across the fermentation broth. The fermentation broth is typically an aqueous nutrient medium comprising micro-organisms, metal and non-metal nutrients. Such liquid nutrient media are suitable electrolytes, wherein electrons can be provided via one or more electrodes.

In particular embodiments, the fermentation must be maintained anaerobic, thus simple electrolysis of water cannot be used as electrolytically generated oxygen can be detrimental to microbial cell functioning. However, electrons can be provided to a fermentation broth via a half cell, wherein the cathode can be placed into the bioreactor and an anode can be placed outside the bioreactor where the generation of oxygen is not detrimental to the fermentation. In such half-cells, the electrical circuit can be maintained by providing a salt bridge and/or permeable membrane to support ion flow.

It is also recognised the methods of the invention may also increase the overall energy efficiency of the fermentation of substrate comprising CO and/or CO2 and optionally H2. These substrates are typically provided in gaseous form and there is a significant energy cost associated with transferring such compounds into solution for conversion into products. However, the energy required to transfer the same amount of reducing equivalents, in the form of electrons, into solution is substantially less.

DEFINITIONS

Unless otherwise defined, the following terms as used throughout this specification are defined as follows:

The term "substrate comprising carbon monoxide" and like terms should be understood to include any substrate in which carbon monoxide is available to one or more strains of bacteria for growth and/or fermentation, for example.

"Gaseous substrate comprising carbon monoxide" include any gas which contains carbon monoxide. The gaseous substrate will typically contain a significant proportion of CO, preferably at least about 5% to about 100% CO by volume.

In the context of fermentation products, the term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. The term "acetate" includes both acetate salt alone and a mixture of molecular or free acetic acid and acetate salt, such as the mixture of acetate salt and free acetic acid present in a fermentation broth as may be described herein. The ratio of molecular acetic acid to acetate in the fermentation broth is dependent upon the pH of the system.

"Electron shuttle mediators" or "Redox mediator(s)" and the like, as used herein is intended to refer to an electron shuttle that acts as a reversible electron donor and/or electron acceptor. Mediators include viologen dyes (such as methyl viologen), anthraquinone and other quinone dyes, triphenylmethane dyes, phthalocyanimes, methine dyes, pyrrole dyes, porphyrin dyes, pteridines, pteridones, flavines, and metal complexes of secondary groups VI, VII and VIII.

The term "bioreactor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Moving Bed Biofilm Reactor (MBBR), Bubble Column, Gas Lift Fermenter, Membrane Reactor such as Hollow Fibre Membrane Bioreactor (HFMBR), Static Mixer, or other vessel or other device suitable for gas-liquid contact.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

While the following description focuses on particular embodiments of the invention, namely the production of ethanol and/or acetate using CO as the primary substrate, it should be appreciated that the invention may be applicable to production of alternative alcohols and/or acids and the use of alternative substrates as will be known by persons of ordinary skill in the art to which the invention relates. For example, gaseous substrates containing carbon dioxide and hydrogen may be used. Further, the invention may be applicable to fermentation to produce butyrate, propionate, caproate, ethanol, propanol and butanol. The methods may also be of use in producing hydrogen. By way of example, these products may be produced by fermentation using microbes from the genus *Moorella*, *Clostridia*, *Ruminococcus*, *Acetobacterium*, *Eubacterium*, *Butyribacterium*, *Oxobacter*, *Methanosarcina*, *Methanosarcina*, and *Desulfotomaculum*.

Fermentation

Certain embodiments of the invention are adapted to use gas streams produced by one or more industrial processes. Such processes include steel making processes, particularly processes which produce a gas stream having a high CO content or a CO content above a predetermined level (i.e., 5%). According to such embodiments, acetogenic bacteria are preferably used to produce acids and/or alcohols, particularly ethanol or butanol, within one or more bioreactors. Those skilled in the art will be aware upon consideration of the instant disclosure that the invention may be applied to various industries or waste gas streams, including those of vehicles with an internal combustion engine. Also, those skilled in the art will be aware upon consideration of the instant disclosure that the invention may be applied to other fermentation reactions including those using the same or different micro-organisms. It is therefore intended that the scope of the invention is not limited to the particular embodiments and/or applications described but is instead to be understood in a broader sense; for example, the source of the gas stream is not limiting, other than that at least a component thereof is usable to feed a fermentation reaction. The invention has particular applicability to improving the overall carbon capture and/or production of ethanol and other alcohols from gaseous substrates comprising CO. Processes for the production of ethanol and other alcohols from gaseous substrates are known. Exemplary processes include those described for example in WO2007/117157, WO2008/115080, WO2009/022925, WO2009/064200; U.S. Pat. No. 6,340,581, U.S. Pat. No. 6,136,577, U.S. Pat. No. 5,593,886, U.S. Pat. No. 5,807,722 and U.S. Pat. No. 5,821,111, each of which is incorporated herein by reference.

A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091), *Clostridium ragsdalei* (WO/2008/028055) and *Clostridium autoethanogenum* (Abrini et al, Archives of Microbiology 161: pp 345-351). Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Moorella thermoacetica*, *Moorella thermoautotrophica*, *Ruminococcus productus*, *Acetobacterium woodii*, *Eubacterium limosum*, *Butyribacterium methylotrophicum*, *Oxobacter pfennigii*, *Methanosarcina barkeri*, *Methanosarcina acetivorans*, *Desulfotomaculum kuznetsovii* (Simpa et. al. Critical Reviews in Biotechnology, 2006 Vol. 26. Pp 41-65). In addition, it should be understood that other acetogenic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 19630. In another embodiment, the *Clostridium autoethanogenum* is a *Clostridium autoethanogenum* having the identifying characteristics of DSMZ deposit number DSMZ 10061.

Culturing of the bacteria used in the methods of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (v) J. L. Vega, et al. (1989). Study of gaseous substrate fermentations: Carbon monoxide conversion to acetate. 1. Batch culture. Biotechnology and Bioengineering. 34. 6. 774-784; (vi) J. L. Vega, et al. (1990). Design of Bioreactors for Coal Synthesis Gas Fermentations. Resources, Conservation and Recycling. 3. 149-160; all of which are incorporated herein by reference.

The fermentation may be carried out in any suitable bioreactor, such as a continuous stirred tank reactor (CSTR), an immobilised cell reactor, a gas-lift reactor, a bubble column reactor (BCR), a membrane reactor, such as a Hollow Fibre Membrane Bioreactor (HFMBR) or a trickle bed reactor (TBR). Also, in some embodiments of the invention, the bioreactor may comprise a first, growth reactor in which the micro-organisms are cultured, and a second, fermentation reactor, to which fermentation broth from the growth reactor is fed and in which most of the fermentation product (e.g. ethanol and acetate) is produced.

According to various embodiments of the invention, the carbon source for the fermentation reaction is a gaseous substrate containing CO. The substrate may be a CO-containing waste gas obtained as a by-product of an industrial process, or from another source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing substrate may be captured from the industrial process before it is emitted into the atmosphere, using any convenient method. Depending on the composition of the CO-containing substrate, it may also be desirable to treat it to remove any undesired impurities, such as dust particles before introducing it to the fermentation. For example, the gaseous substrate may be filtered or scrubbed using known methods.

Alternatively, the CO-containing substrate may be sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention.

The CO-containing substrate will typically contain a major proportion of CO, such as at least about 20% to about 100% CO by volume, from 40% to 95% CO by volume, from 60% to 90% CO by volume, and from 70% to 90% CO by volume. In particular embodiments, the substrate comprises 25%, or 30%, or 35%, or 40%, or 45%, or 50% CO by volume. Substrates having lower concentrations of CO, such as 6%, may also be appropriate, particularly when $H_2$ and $CO_2$ are also present.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of H2:CO. In other embodiments, the substrate stream comprises low concentrations of H2, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In particular embodiments, the substrate stream comprises CO2 and no or minimal CO.

Typically, the carbon monoxide will be added to the fermentation reaction in a gaseous state. However, the methods of the invention are not limited to addition of the substrate in this state. For example, the carbon monoxide can be provided in a liquid. For example, a liquid may be saturated with a carbon monoxide containing gas and that liquid added to the bioreactor. This may be achieved using standard methodology. By way of example a microbubble dispersion generator (Hensirisak et. al. Scale-up of microbubble dispersion generator for aerobic fermentation; *Applied Biochemistry and Biotechnology* Volume 101, Number 3/October, 2002) could be used for this purpose.

It will be appreciated that for growth of the bacteria and CO-to-alcohol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438, WO2007/117157, WO2008/115080, WO2009/022925, WO2009/058028, WO2009/064200, WO2009/064201 and WO2009/113878, referred to above. The present invention provides a novel media which has increased efficacy in supporting growth of the micro-organisms and/or alcohol production in the fermentation process. This media will be described in more detail hereinafter.

The fermentation should desirably be carried out under appropriate conditions for the desired fermentation to occur (e.g. CO-to-ethanol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. Suitable conditions are described in WO02/08438, WO07/117,157, WO08/115,080 and WO2009/022925.

The optimum reaction conditions will depend partly on the particular micro-organism used. However, in general, it is preferred that the fermentation be performed at pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Also, since a given CO-to-ethanol conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per litre per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

Product Recovery

The products of the fermentation reaction can be recovered using known methods. Exemplary methods include those described in WO07/117,157, WO08/115,080, U.S. Pat. No. 6,340,581, U.S. Pat. No. 6,136,577, U.S. Pat. No. 5,593,886, U.S. Pat. No. 5,807,722 and U.S. Pat. No. 5,821,111. However, briefly and by way of example only ethanol may be recovered from the fermentation broth by methods such as fractional distillation or evaporation, and extractive fermentation.

Distillation of ethanol from a fermentation broth yields an azeotropic mixture of ethanol and water (i.e., 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non volatile and is recovered for re-use in the fermentation.

Acetate, which is produced as a by-product in the fermentation reaction, may also be recovered from the fermentation broth using methods known in the art.

For example, an adsorption system involving an activated charcoal filter may be used. In this case, it is preferred that microbial cells are first removed from the fermentation broth using a suitable separation unit. Numerous filtration-based methods of generating a cell free fermentation broth for product recovery are known in the art. The cell free ethanol- and acetate-containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are also known in the art and may be used in the processes of the present invention. For example, U.S. Pat. Nos. 6,368,819 and 6,753,170 describe a solvent and cosolvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented micro-organisms in order to extract the acetic acid product. The solvent/co-solvent containing the acetic acid product is then separated from the broth by distillation. A second distillation step may then be used to purify the acetic acid from the solvent/co-solvent system.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more product from the broth simultaneously or sequentially. In the case of ethanol it may be conveniently recovered by distillation, and acetate may be recovered by adsorption on activated charcoal, using the methods described above. The separated microbial cells are preferably returned to the fermentation bioreactor. The cell free permeate remaining after the ethanol and acetate have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Electrochemical Fermentation

In accordance with the invention, there is provided a method of improving efficiency of carbon capture in carboxydotrophic fermentation via the Wood-Ljungdahl pathway, the method including applying an electrical potential across the fermentation. An electrical potential can be applied across a fermentation by any means known to those skilled in the art. For example, a know means for applying an electrical potential is an electrochemical cell. In particular, an electrochemical cell suitable for use with the methods of the invention is an electrolytic cell. In accordance with the invention, fermentation is typically conducted with a fermentation broth comprising one or more micro-organisms and an aqueous nutrient media comprising essential nutrients including metal ions. As such, the liquid nutrient media provides an ideal electrolyte for electrolysis. Accordingly, a potential can be applied by providing electrodes connected to an electrical circuit.

In particular embodiments of the invention, the micro-organism is anaerobic and must be maintained substantially oxygen free. In electrolysis, wherein both electrodes extend into an electrolyte; oxygen will form at the anode through dissociation of water. This would be detrimental to the microbial culture. As such, in particular embodiments, the method includes applying an electrical potential across the fermentation through a half-cell, wherein the anode is separated from the fermentation broth via an ion permeable membrane or alternative salt bridge. In such embodiments, the oxygen can be discharged without detriment to the microbial culture.

In accordance with the invention, the electrical potential applied to the fermentation increases efficiency of carbon fixation. In particular embodiments of the invention, a carboxydotrophic bacteria will fix at least a portion of a substrate comprising CO and/or CO2 into cell mass and/or products such as ethanol. The energy required to fix the carbon is generally labelled 'reducing equivalents' and can be derived through oxidation of a number of reduced entities. Carboxydotrophic bacteria such as *Clostridium autoethanogenum* typically derive reducing equivalents through oxidation of CO and/or H2. However, in accordance with the invention, efficiency of carbon fixation is improved through application of a potential across a fermentation. In accordance with the invention, carbon is fixed as cell mass and products such as ethanol with a lower requirement for CO and/or H2 as reducing equivalents. Thus, application of a potential across a carboxydotrophic fermentation decreases the amount of CO2 produced per amount of carbon fixed as cell mass and/or products. Typically, when a potential is applied across a fermentation, one or more electron shuttle mediators, such benzyl viologen or methyl viologen present in the fermentation broth, are reduced. These mediators, in turn, assist in reduction of a microbial cells reduction machinery, such as the Ferredoxin$_{ox/red}$ couple or the NAD(P)H/NAD(P) couples. Thus in accordance with particular embodiments of the invention, one or more electron shuttle mediators is provided in the fermentation broth. However, in particular embodiments, the method proceed without the need of electron shuttle mediators.

It has also been recognised that application of a potential can also alter how the micro-organism(s) fix carbon. In example provided herein, application of a potential across a fermentation increases the proportion of carbon directed toward cell mass and as such increases microbial growth. In particular embodiments, microbial growth is increased by at least 5%, or at least 10%, or at least 15%, or at least 20%.

Those skilled in the art will appreciate how to determine the potential necessary to improve efficiency of carbon fixation and/or improve microbial growth. However, by way of example, a direct current with a voltage of up to 20V may be applied across the electrodes. In particular embodiments, a potential of at least 2V, or at least 4V, or at least 6V, or at least 8V, or at least 10V, or at least 15V, or at least 20V is applied. In particular embodiments of the invention, the potential can be controlled such that a substantially constant current through the electrolyte is maintained at approximately 1 mA, or approximately 2 mA, or approximately 3 mA, or approximately 4 mA, or approximately 5 mA, or approximately 6 mA, or approximately 7 mA, or approximately 8 mA, or approximately 9 mA, or approximately 10 mA. Again, those skilled in the art will appreciate how to determine an optimum current, which may change over time and may be different for different micro-organisms.

In another embodiment of the invention, there is provided an electrochemical bioreactor comprising means for introducing a substrate comprising CO and/or CO2 and optionally H2 to a fermentation broth and means for applying a potential across the fermentation broth. In particular embodiments, the means for applying a potential is controllable, such that a desired current can be maintained through the fermentation broth.

Figure 2:
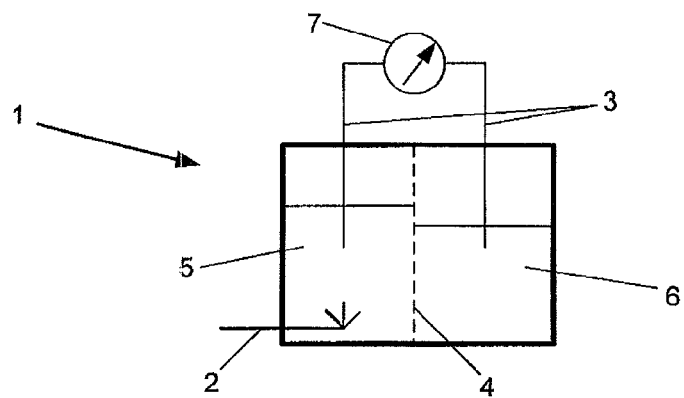
FIG. 2 is a plan view of a bioreactor having a means for applying an electrical potential in accordance with one embodiment of the present invention.

FIG. 2 shows an electrochemical bioreactor according to a particular embodiment of the invention. The bioreactor 1, includes means for supplying a gaseous substrate (2) and means for applying a potential across a fermentation. In particular embodiments, the fermentation is anaerobic, therefore the electrochemical bioreactor comprises two electrodes 3 separated by an ion permeable separator 4. The ion permeable separator can be a porous membrane or ceramic material or other suitable material known in the art. In use, a portion of the bioreactor 5 can be filled with a fermentation broth comprising one or more microorganisms and a liquid nutrient media. In use, another portion of the bioreactor 6 can be filled with a conductive salt solution. Electrodes 3 are configured such that, in use; they can extend into the fermentation broth and the conductive salt solution. The bioreactor also comprises an electrical circuit and means to control a potential (7) across the electrodes.

EXAMPLES

Materials and Methods

| Solution A | | | |
|---|---|---|---|
| NH$_4$Ac | 3.083 g | KCl | 0.15 g |
| MgCl$_2$•6H$_2$O | 0.61 g | | |
| CaCl$_2$•2H$_2$O | 0.294 g | Distilled Water | Up to 1 L |

| Solution(s) B | | | |
|---|---|---|---|
| Component | mol/L H2O | Component | mol/L H2O |
| FeCl$_3$ | 0.1 | Na$_2$MoO$_4$ | 0.01 |
| CoCl$_2$ | 0.05 | ZnCl$_2$ | 0.01 |
| NiCl$_2$ | 0.05 | MnCl2 | 0.01 |
| H$_3$BO$_3$ | 0.01 | NTA | 0.3 |
| Na$_2$SeO$_3$ | 0.01 | | |

| Solution C | | | |
|---|---|---|---|
| Biotin | 20.0 mg | Calcium D-(*)- pantothenate | 50.0 mg |
| Folic acid | 20.0 mg | | |
| Pyridoxine•HCl | 10.0 mg | Vitamin B12 | 50.0 mg |
| Thiamine•HCl | 50.0 mg | p-Aminobenzoic acid | 50.0 mg |
| Riboflavin | 50.0 mg | Thioctic acid | 50.0 mg |
| Nicotinic acid | 50.0 mg | Distilled water | To 1 Litre |

Preparation of Cr (II) Solution

A 1 L three necked flask was fitted with a gas tight inlet and outlet to allow working under inert gas and subsequent transfer of the desired product into a suitable storage flask. The flask was charged with CrCl$_3$.6H$_2$O (40 g, 0.15 mol), zinc granules [20 mesh] (18.3 g, 0.28 mol), mercury (13.55 g, 1 mL, 0.0676 mol) and 500 ml of distilled water.

Following flushing with N$_2$ for one hour, the mixture was warmed to about 80° C. to initiate the reaction. Following two hours of stirring under a constant N$_2$ flow, the mixture was cooled to room temperature and continuously stirred for another 48 hours by which time the reaction mixture had turned to a deep blue solution. The solution was transferred into $N_2$ purged serum bottles and stored in the fridge for future use.

Bacteria: *Clostridium autoethanogenum* used is that deposited at the German Resource Centre for Biological Material (DSMZ) and allocated the accession number DSMZ 19630.

Sampling and Analytical Procedures

Media samples were taken from the CSTR reactor at intervals over periods up to 20 days. Each time the media was sampled care was taken to ensure that no gas was allowed to enter into or escape from the reactor.

HPLC:

HPLC System Agilent 1100 Series. Mobile Phase: 0.0025N Sulfuric Acid. Flow and pressure: 0.800 mL/min. Column: Alltech IOA; Catalog #9648, 150×6.5 mm, particle size 5 μm. Temperature of column: 60° C. Detector: Refractive Index. Temperature of detector: 45° C.

Method for Sample Preparation:

400 μl of sample and 50 μL of 0.15M $ZnSO_4$ and 50 μL of 0.15M $Ba(OH)_2$ are loaded into an Eppendorf tube. The tubes are centrifuged for 10 min. at 12,000 rpm, 4° C. 200 μL of the supernatant are transferred into an HPLC vial, and 5 μL are injected into the HPLC instrument.

Headspace Analysis:

Measurements were carried out on a Varian CP-4900 micro GC with two installed channels. Channel 1 was a 10 m Molsieve column running at 70° C., 200 kPa argon and a backflush time of 4.2 s, while channel 2 was a 10 m PPQ column running at 90° C., 150 kPa helium and no backflush. The injector temperature for both channels was 70° C. Runtimes were set to 120 s, but all peaks of interest would usually elute before 100 s.

Example 1

Batch Fermentation in CSTR

Two 2 L CSTR's (A) and (B) were set up under the following conditions: Media was prepared as follows: 85% $H_3PO_4$ (30 mM) was added to 1.5 L of solution A. The pH of the media was adjusted to 5.3 by the addition of NH4OH. The media solution was sterilised by autoclaving for 30 minutes at 121° C., or by filter sterilisation prior to use. Resazurin was added as a redox indicator. The media solution was aseptically and anaerobically transferred into a 1.5 L CSTR vessel, and continuously sparged with $N_2$. Once transferred to the fermentation vessel, the reduction state and pH of the transferred media could be measured directly via probes. The media was heated to 37° C. and stirred at 300 rpm.

Sodium sulfide solution (3.75 mL of a 0.2M solution) was added, followed by trace metal solution B (1.5 mL), Na2WO4 (1.5 mL of a 0.01M solution) then Solution C (15 mL). ORP of the solution was adjusted to approx −200 mV using Cr(II) solution.

Fermenter B was converted to an electrochemical bioreactor by modifying the CSTR with two stainless steel electrodes. The cathode extended into the liquid nutrient medium while the anode extended into a half-cell vessel separated from the liquid nutrient medium by an ion permeable membrane. The anode half-cell vessel contained a 3M solution of KCl. Direct current was applied across the electrodes with a potential of 10-15V, such that the current was maintained at approximately 7 mA throughout the fermentation.

Prior to inoculation, the gas was switched to a blend of 2% H2, 33% N2, 44% CO, 21% CO2 and 100% H2. An actively growing *Clostridium autoethanogenum* culture was inoculated into the CSTR at a level of approximately 10% (v/v). During this experiment, Na2S solution was added at a rate of approx 0.16 mMol/day. The fermenters were operated under substantially similar conditions and substrate supply was increased in response to the requirements of each microbial culture to compare the control fermenter (A) with the electrochemical bioreactor (B).

| Fermenter | Day | Biomass (g/L) | Ethanol (g/L) | Total CO uptake (mmol/L) | Total CO2 production (mmol/L) | $CO2_{produced}/CO_{consumed}$ ratio |
|---|---|---|---|---|---|---|
| A | 0.6 | 0.60* | 1.0* | 382 | 252 | 0.66 |
|   | 0.8 | 0.78* | 1.9* | 604 | 398 | 0.66 |
|   | 1.0 | 1.02  | 3.8  | 850 | 563 | 0.66 |
|   | 1.2 | 1.28* | 5.7* | 1121 | 749 | 0.67 |
|   | 1.4 | 1.59* | 7.6* | 1427 | 962 | 0.67 |
|   | 1.6 | 1.90* | 9.5* | 1783 | 1209 | 0.68 |
|   | 1.8 | 2.12  | 12.1 | 2205 | 1500 | 0.68 |
|   | 2.0 | 2.40  | 14.9 | 2711 | 1848 | 0.68 |
| B | 0.6 | 0.70* | 1.0* | 591 | 272 | 0.46 |
|   | 0.8 | 0.82* | 1.8* | 753 | 366 | 0.49 |
|   | 1.0 | 1.16  | 3.3  | 940 | 483 | 0.51 |
|   | 1.2 | 1.51* | 5.0* | 1173 | 638 | 0.54 |
|   | 1.4 | 1.80* | 6.9* | 1470 | 837 | 0.57 |
|   | 1.6 | 2.18* | 8.7* | 1844 | 1090 | 0.59 |
|   | 1.8 | 2.61  | 10.9 | 2308 | 1403 | 0.61 |
|   | 2.0 | 3.00  | 13.7 | 2869 | 1778 | 0.62 |

*Extrapolated from graphical plot of fermentation parameters

The CO2 produced in electrochemical bioreactor (B) was substantially less than that produced in (A) throughout the fermentation. This indicates that less CO was used for production of reducing equivalents in (B) than in (A). This is unexpected, as the microbial growth and metabolite production are similar. It is considered that electrons available in electrochemical bioreactor (B) offset the amount of reducing equivalents required to fix a certain amount of carbon as microbial cell mass and/or products. Another surprising outcome is that microbial growth in the electrochemical bioreactor (B) exceeded fermenter (A) by approximately 20%, whereas ethanol production was slightly reduced.

The invention has been described herein with reference to certain preferred embodiments, in order to enable the reader to practice the invention without undue experimentation. Those skilled in the art will appreciate that the invention is susceptible to variations and modifications other than those specifically described. It is to be understood that the invention includes all such variations and modifications. Furthermore, titles, heading, or the like are provided to enhance the reader's comprehension of this document, and should not be read as limiting the scope of the present invention. The entire disclosures of all applications, patents and publications cited above and below, if any, are herein incorporated by reference.

The reference to any prior art in this specification is not, and should not be taken as, an acknowledgement or any form of suggestion that that prior art forms part of the common general knowledge in the field of endeavour in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

The invention claimed is:

1. A method for the microbial fermentation of a gaseous substrate selected from the group consisting of carbon monoxide (CO) and CO plus hydrogen ($H_2$), the method comprising contacting the gaseous substrate with a fermentation broth comprising a carboxydotrophic bacteria in a bioreactor operated at fermentation reaction conditions and applying an electrical potential across the fermentation broth to produce products comprising alcohols, acids or mixtures thereof.

2. The method of claim 1, wherein the electrical potential is applied across a cathode and an anode electrode to generate a direct current therebetween, the cathode electrode being immersed in the fermentation broth and the anode electrode being immersed in an electrolyte outside the fermentation broth and the electrolyte and fermentation broth are connected by a salt bridge or an ion permeable membrane.

3. The method of claim 1, wherein the electrical potential is at least 2V.

4. The method of claim 2, wherein the voltage is controlled to enable a substantially constant current through the fermentation broth.

5. The method of claim 4, wherein the current is maintained at above 1 mA.

6. The method of claim 1, wherein one or more electron shuttle mediators is provided in the fermentation broth.

7. The method of claim 1, wherein applying the electrical potential increases growth of the bacteria by at least 5%.

* * * * *